United States Patent [19]

Kobayashi et al.

[11] Patent Number: 4,992,533
[45] Date of Patent: Feb. 12, 1991

[54] SULFATED OLIGOSACCHARIDES AND DERIVATIVES THEREOF

[75] Inventors: Masanori Kobayashi; Mamoru Sugimoto; Kenkichi Tomita; Yukishige Ito, all of Tokyo; Tomoya Ogawa, Musashino, all of Japan

[73] Assignees: Rikagaku Kenkyusho, Saitama; Mect Corporation, Tokyo, both of Japan

[21] Appl. No.: 413,441

[22] Filed: Sep. 27, 1989

[30] Foreign Application Priority Data

Sep. 29, 1988 [JP] Japan ................. 63-245748

[51] Int. Cl.$^5$ .......................... C07G 3/00; C07H 17/00; C07H 19/00; C08B 37/00
[52] U.S. Cl. ........................................ 536/4.1; 536/54; 536/17.5; 536/17.9; 536/17.6; 536/17.2; 536/22
[58] Field of Search ................. 536/4.1, 18.6, 18.5, 536/17.9, 17.4, 17.6, 124, 18.7, 54, 55.1, 55.3, 21, 17.5, 17.2

[56] References Cited

U.S. PATENT DOCUMENTS

| | | | |
|---|---|---|---|
| 4,415,490 | 11/1983 | Joh | 536/21 |
| 4,607,025 | 8/1986 | Petitou et al. | 536/4.1 |
| 4,675,392 | 6/1987 | Dahmen et al. | 536/17.9 |
| 4,818,816 | 4/1989 | Petitou et al. | 536/55.3 |

OTHER PUBLICATIONS

Bo Nilsson et al., "Structure of Oligosaccharides and the Linkage Region Between Keratan Sulfate and the Core Proteoglycans from Monkey Cornea", *Journal of Biological Chemistry*, 258:10:6056–6063, 1983.

Peter Scudder et al., "Isolation and Characterization of Sulphated Oligosaccharides Released from Bovine Corneal Keratan Sulphate by the Action of Endo-β-Galactosidase", *Eur. J. Biochem.*, 157:365–373, 1986.

Maurice Petitou et al., "Synthesis of Heparin Fragments: A Methyl α-Pentaoside with High Affinity for Antithrombin III", *Carbohydrate Research* 167:67–75, 1987.

Nilsson et al. "Structure of Oligosaccharides and the Linkage Region between Keratan Sulfate and the Core Protein on Proteoglycans from Monkey Cornea", *J. Biol. Chem.*, 258, pp. 6056–63 (1983).

Scudder et al. "Isolation and Characterization of Sulphated Oligosaccharides Released from Bovine Corneal Keratan Sulphate by the Action of Endo-β-galactosidase", *Eur. J. Chem.*, 157, pp. 365–73 (1986).

Petitou et al. "Synthesis of Heparin Fragments: A Methyl α-Pentaoside With High Affinity for Antithrombin III", *Carbo. Res.*, 167, pp. 67–75 (1987).

*Primary Examiner*—Ronald W. Griffin
*Assistant Examiner*—Everett White
*Attorney, Agent, or Firm*—Seed and Berry

[57] ABSTRACT

The present invention relates to sulfated oligosaccharides or their derivatives such as the following compound and being useful for diagnosing or treating diseases such as immunity-related diseases and mucopolysaccharide diseases.

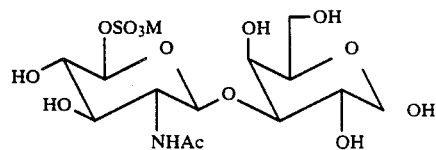

(M is an alkali metal).

2 Claims, No Drawings

SULFATED OLIGOSACCHARIDES AND DERIVATIVES THEREOF

BACKGROUND OF THE INVENTION

1. Field of the Invention

The present invention relates to sulfated oligosaccharides and their derivatives.

2. Description of Prior Art

Keratan sulfate, which is a kind of glycosaminoglycans (mucopolysaccharides), is contained, in a large amount, in the cornea, discus intervertebralis, cartilago and arteria of mamals.

Keratan sulfate contains, as a repeating unit, a disaccharide comprised of D-galactose and N-acetylglucosamine-6-sulfate, and is treated with, for example, endo-$\beta$-galactosidase to produce sulfated oligosaccharides.

It was reported that sulfated oligosaccharides have a site which an antibody can recognize [J. Cell Biology, 101, 53 (1985)]. Further, sulfated oligosaccharides have been confirmed to be largely related to diseases such as polysaccharide disease caused by accumulation of mucopolysaccharide.

SUMMARY OF THE INVENTION

The object of the present invention is to provide sulfated oligosaccharides and their derivatives which are useful for diagnosing or treating diseases such as immuno disorder and mucopolysaccharidosis.

The present inventors have made intensive studies to accomplish the above object, and found out that this object can be attained by the present invention.

Namely, the present invention relates to sulfated oligosaccharides or their derivatives having the following general formula:

[structure with $R_1O$, $R_2O$, $OR_4$, $R_3$, $R_5$]

wherein,

① $R_1=R_2=C_6H_5CH_2(Bn)$, $R_3 = $ —N(phthalimide) (NPhth), $R_4 = $ —C$_6$H$_4$—OCH$_3$(MP) and $R_5 = $ OH,

[allyl ether structure], [trichloroacetimidate structure $O-C(=NH)CX_3$]

(wherein, X=a halogen atom) or

[structure with OBn groups]

② $R_1=R_2=Bn$, $R_3=NHAc$(Ac=an acetyl group), $R_4=H$, MP or SO$_3$M (wherein, M=an alkali metal) and $R_5 = $ [structure with OBn groups],

③

$R_1 = $ [structure with $OR_6$, allyl groups]

(wherein, $R_6=Ac$, Bn or H), $R_2=Bn$, $R_3=NPhth$, $R_4=MP$ and $R_5=$

[allyl ether structure],

④

$R_1 = $ [structure with HO, OBn, OH], $R_2=Bn$, $R_3=NPhth$, $R_4=MP$ and $R_5=OH$,

⑤

$R_1 = $ [structure with AcO, OBn, OAc], $R_2=Bn$, $R_3=NPhth$, $R_4=MP$ and $R_5=OAc$, OH,

[allyl ether structure], [trichloroacetimidate structure $O-C(=NH)CX_3$]

(X is a halogen atom) or

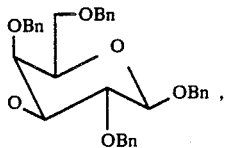

(6)

$R_1 =$ 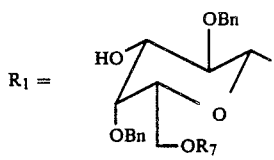

wherein
$R_7 =$ H or t-Bu($C_6H_5$)$_2$Si-(TBDPS)
$R_2 =$ Bn, $R_3 =$ NPhth, $R_4 =$ MP and $R_5 =$ 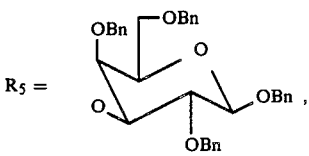

(7)

$R_1 =$ 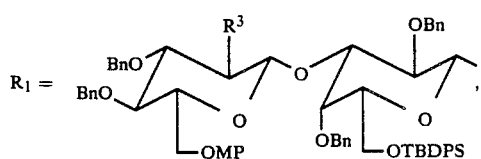

$R_2 =$ Bn, $R_3 =$ NPhth or NHAc, $R_4 =$ MP and $R_5 =$

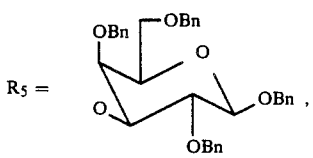

(8)

$R_1 =$ 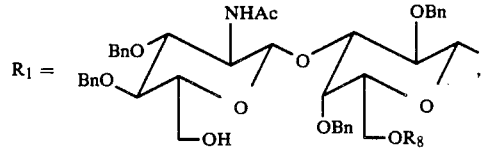

(wherein, $R_8 =$ H or TBDPS), $R_2 =$ Bn, $R_3 =$ NHAc, $R_4 =$ H and $R_5 =$ 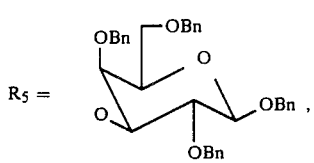

(9)

$R_1 =$ 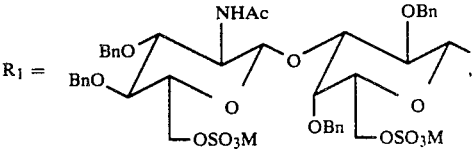

(wherein M=an alkali metal), $R_2 =$ Bn, $R_3 =$ NHAc, $R_4 =$ SO$_3$M and $R_5 =$ 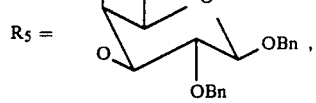

and (10)

$R_1 =$ 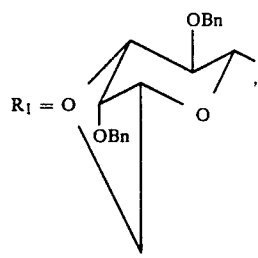

$R_2 =$ Bn, $R_3 =$ NPhth, $R_4 =$ MP and $R_5 =$ 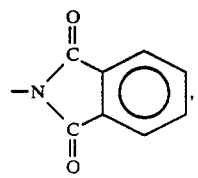

The present invention will be explained in more detail below.

Compound (8) having the following formula (8):

$R_5 =$ (structure)

wherein Bn is a benzyl group, NPhth is (phthalimido structure)

and MP is a p-methoxyphenyl group, can be synthesized as follows.

Compound (6) having the following general formula (6):

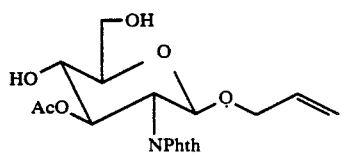

(6)

wherein Ac is an acetyl group, is reacted with p-methoyphenol at −10~70° C. for 1 hr. to 1 day in the presence of phosphines such as triphenylphosphine (Ph3P), P(PhCH3)3, tributyl phosphine and triethylphosphine and in a halogenated solvent such as dichloromethane, chloroform, carbon tetrachloride and 1,2-dichloroethane, to produce Compound (7) having the following general formula (7):

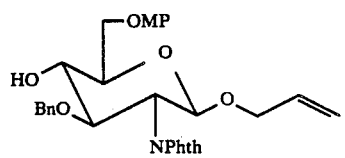

(7)

then reacting Compound (7) with a benzyl halide such as benzylchloride. The benzylation reaction is conducted at −10~70° C. for 10 min. to 1 day in the presence of a catalyst such as Ag2O, KI, NaI and KaH and in a solvent such as DMF, to produce Compound (8).

Incidentally, Compound (6) is produced from commercially available Compound (1) according to Scheme 1 as below.

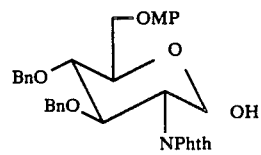

(9)

is obtained from Compound (8) in two steps. In the first step, Compound (8) is treated with RhCl [P(C6H5)3]3, 1,4-d iazabicyclo[2.2.2.]octane (DABCO) or triethylamine at 0~100° C. for 1 hr. to 1 day in a solvent such as ethanol/benzene/water (7:3:1) and CH3CN/ethanol/water. In the second step, the resulting compound is treated at 0~70° C. for 10 min. to 1 day in the presence of HgO, HgCl2, HgBr2, HgI2 or I2 and in a medium such as acetone/water (9:1), THF/water and CH3CN/water.

Compound (10) having the following general formula (10):

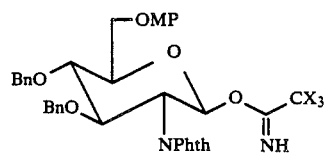

(10)

wherein X is a halogen atom, is obtained by treating Compound (9) at −20~40° C. for 30 min.~8 hr. in the presence of a catalyst such as CCl3CN/1,8-diazabicyclo[5.4.0.]undece-7-ene (DBU), CCl3CN/NaH, CCl3CN/Na2CO3 and CCl3CN/K2CO3 and in a solvent such as CH2Cl2, ClCH2CH2Cl, toluene, CCl, and CHCl3.

Compound (9) having the following general formula (9):

Compound (12) having the following general formula (12):

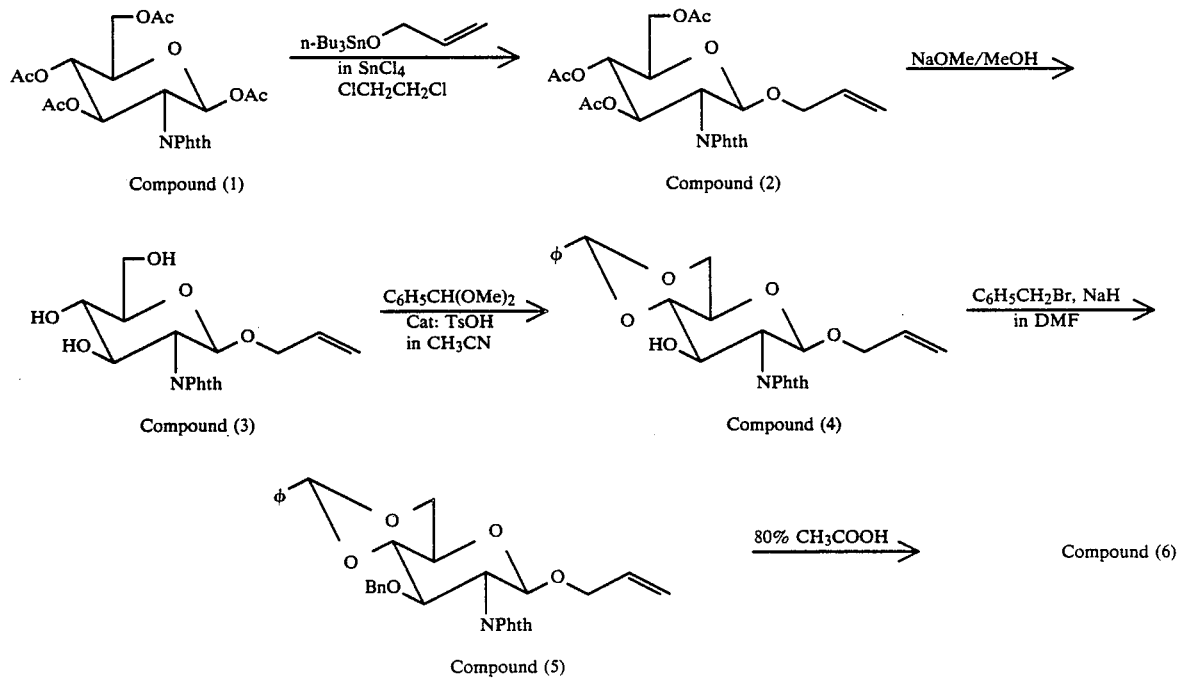

Scheme 1

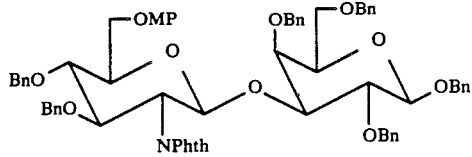
(12)

is obtained by reacting Compound (10) with Compound (11) having the following general formula (11):

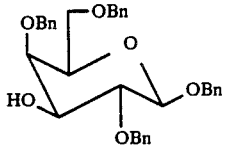
(11)

at $-78 \sim 60°$ C. for 30 min. $\sim 1$ day in the presence of a catalyst such as $BF_3$. $OEt_2$, trimethylsilytriflate (TMSOTf), $TiCl_4$, $SnCl_4$ and methyltriflate and in a solvent such as $ClCH_2CH_2Cl$, $CH_2Cl_2$, toluene, benzene, $CHCl_3$, $CCl_4$, nitromethane, diethylether and tetrahydrofurane.

Compound (13) having the following general formula (13):

(13)

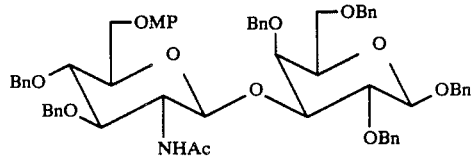

is obtained by treating Compound (12) with $NH_2NH_2.H_2O$, n-$BuNH_2$ and methylamine at 50° C. $\sim$ reflux temperature for 1 hr. $\sim$ 1 day in a solvent such as ethanol and methanol, and then treating the resulting compound with an acetylating agent such as acetic anhydride and acetyl chloride at $0 \sim 70°$ C. for 10 min. $\sim$ 1 day in a solvent such as pyridine, methanol, triethylamine and dimethylaminopyridine.

Compound (14) having the following general formula (14):

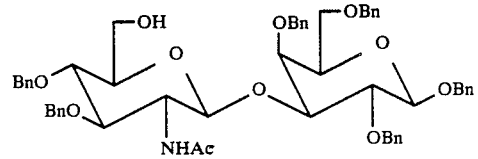
(14)

is obtained by treating Compound (13) at $-20 \sim 70°$ C. for 10 min. $\sim 1$ day in the presence of a catalyst such as ceric ammonium nitrate (CAN) and in a solvent such as $CH_3CH$/water (9:1), THF/water and dioxane/water.

Compound (15) having the following general formula (15):

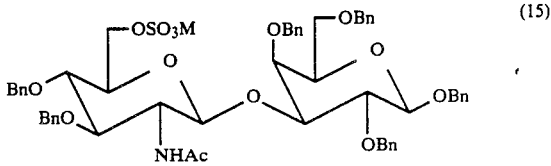
(15)

wherein M is an alkali metal is obtained by treating Compound (14) at $0 \sim 80°$ C. for 30 min. $\sim 1$ day in the presence of $SO_3.N(C_2H_5)_3$ or $SO_3$-pyridine and in a medium such as dimethylformamide (DMF) and pyridine. Incidentally, naturally occurring compound (16) having the following general formula (16):

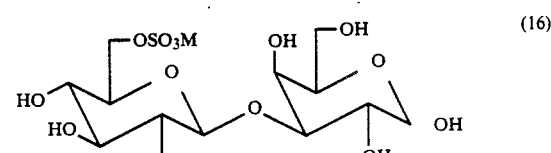
(16)

is obtained by treating Compound (15) at $0 \sim 80°$ C. for 1 hr. $\sim 1$ week in the presence of a catalyst such as 10%-Pd/C, 5%-Pd/C, $PtO_2$ and $Pd(OH)_2$ and in a solvent such as methanol/water, methanol and methanol/acetic acid.

Compound (24) having the following general formula (24):

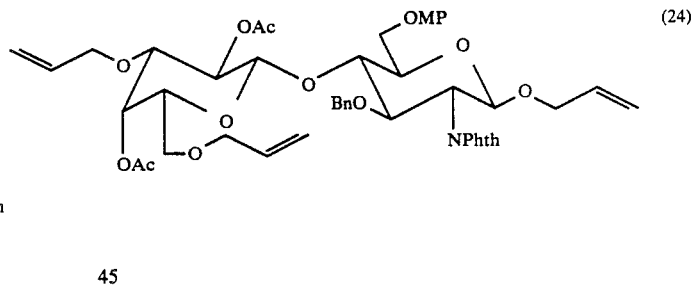
(24)

is produced by reacting Compound (7) with Compound (23) having the following general formula (23):

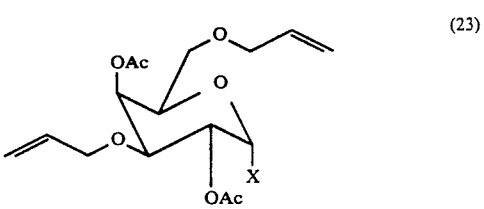
(23)

wherein X is a halogen atom. The reaction is conducted at $-78 \sim 70°$ C. for 10 min. $\sim 1$ day in the presence of a catalyst such as silver triflate (AgOTf), $Sn(OTf)_2$, $AgClO_4$, $AgCO_3$, n-$Bu_4NI$, $HgBr_2$-$Hg(CN)_2$ and silver silicate, and in a solvent which is conventionally used in the glucosidation reaction, such as $ClCH_2CH_2Cl$, $CCl_4$, THF, toluene, benzene, ether, $CHCl_3$ and $CH_2Cl_2$.

In this connection, Compound (23) is produced as follows form Compound (17) having the following general formula (17):

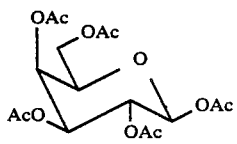 (17)

and being commercially available.

Compound (17) is reacted with n-Bu$_3$SnOCH$_2$CX$_3$ (X is for example Cl) in the presence of a catalyst like SnCl$_4$ and in a solvent like ClCH$_2$CH$_2$Cl, to produce Compound (18) having the following general formula (18):

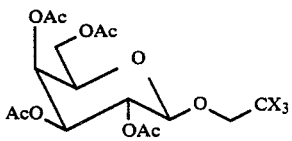 (18)

Compound (18) is then deacetylated with, for example NaOC$_2$H$_5$/C$_2$H$_5$OH, to produce Compound (19) having the following general formula (19):

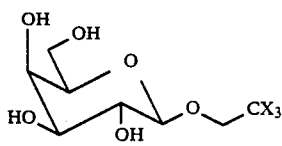 (19)

Compound (19) is treated with (n-Bu$_3$Sn)$_2$O in a solvent such as toluene and then treated with n-Bu$_4$NBr and

to produce Compound (20) having the following general formula (20):

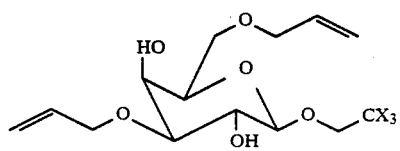 (20)

Compound (20) is then reacted with an acetylating agent such as acetic anhydride in the presence of a catalyst such as DMAP and in an acetylating solvent such as pyridine, to produce Compound (21) having the following general formula (21):

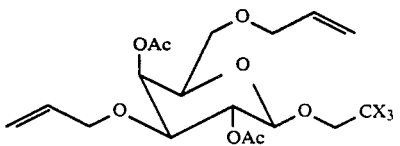 (21)

Compound (21) is then treated with Zn, in example, THF/acetic acid, to produce Compound (22) having the following general formula (22):

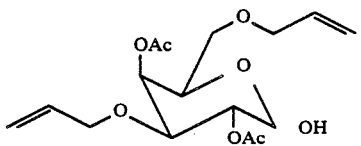 (22)

Compound (22) is then reacted with, for example, SOCl$_2$ in the presence of a catalyst of DMF and in a solvent such as CH$_2$Cl$_2$, to produce Compound (23).

Compound (25) having the following general formula (25):

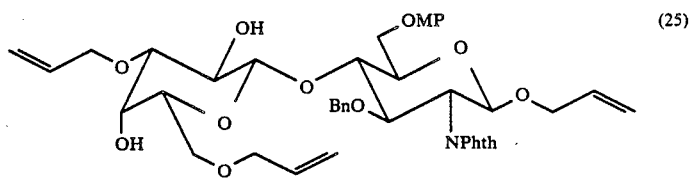 (25)

is produced by treating Compound (24) at $-20 \sim 50°$ C. for 15 min. $\sim 50$ hr. in the presence of LiOH-H$_2$O$_2$, NaOC$_2$H$_5$, NaOH and the others of conventionalloy used alkaline materials and in a solvent such as THF, ether, methanol, methanol/water and ethanol to conduct the deacetylation.

Compound (26) having the following general formula (26):

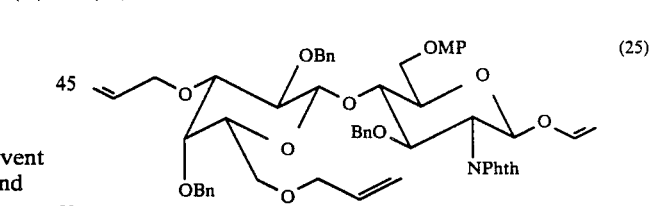 (25)

is produced by treating Compound (25) with a benzylating agent like C$_6$H$_5$CH$_2$Br at $-20 \sim 50°$ C. for 30 min. $\sim 1$ day in the presence of a catalyst such as Ag$_2$O, Ki, NaH and NaI and in a medium like DMF.

Compound (27) having the following general formula (27):

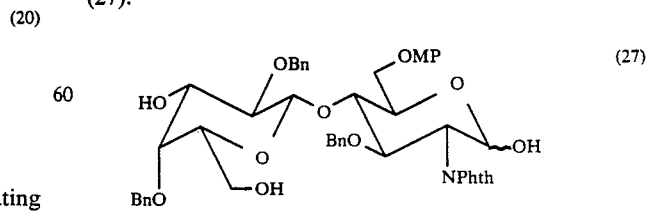 (27)

is produced by treating Compound (26) with RhCl[P(C$_6$H$_5$)$_3$]$_3$, DABCO, triethylamine and the others of conventionally used amine at room temperature to reflux temperature for 1 hr. ~1 day in a solvent like ethanol/benzene/water and CH₃CN/ethanol/water, and then treating the resulting compound at 0~70° C. for 10 min. ~1 day in the presence of a catalyst such as HgCl₂, HgO, I₂, HgBr₂ and HgI₂ and in a solvent like acetone/water, THF/water and CH₃CN/water.

Compound (28) having the following general formula (28):

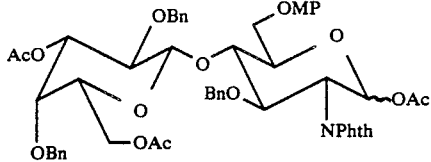

is produced by treating Compound (27) with an acetylating agent such as acetic anhydride at 0~70° C. for 10 min. ~1 day in the presence of a catalyst like DMAP and in a solvent like pyridine. In this reaction, Compound (40) having the following general formula (40):

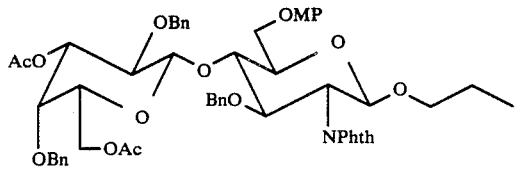

is produced as a by-product.

Compound (29) having the following general formula (29):

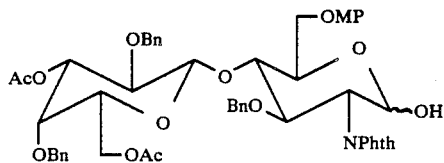

is produced by treating Compound (28) at 20~80° C. for 5 min. ~3 hr. in the presence of a catalyst such as NH₂NH₂.AcOH and in a solvent such as DMF, CH₂Cl₂ and ClCH₂CH₂Cl.

Compound (30) having the following general formula (30):

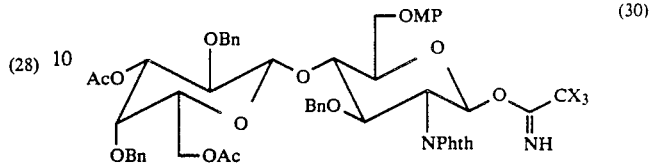

is produced by treating Compound (29) with CCl₃CN/DBU, CCl₃CN/NaH or CCl₃CN/NaCO₃ at −20~40° C. for 30 min. ~8 hr. in a solvent such as CH₂Cl₂, ClCH₂CH₂Cl, toluene, benzene, CCl₄ and CHCl₃.

Compound (31) having the following general formula (31):

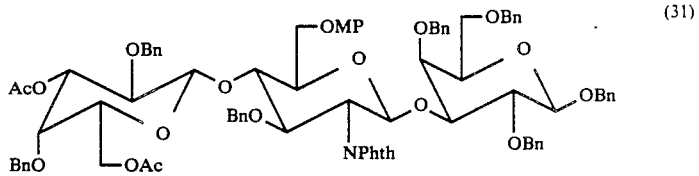

is produced by reacting Compound (30) with Compound (11) at −50~70° C. for 30 min. ~1 day in the presence of a catalyst such as BF₃.OEt₂, TMS triflate, TiCl₄, methyltriflate and SnCl₄ and in a solvent such as ClCH₂CH₂Cl, CH₂Cl₂, toluene, benzene, CHCl₃, CCl₄, nitromethane, ethylether and THF.

Compound (32) having the following general formula (32):

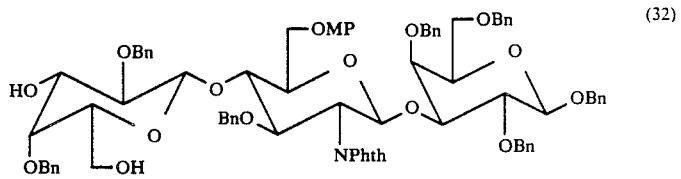

is produced by treating Compound (31) with either (1) LiOH/H₂O₂, NaOMe, NaOH and so on at −20~50° C. for 30 min. ~78 hr. in a solvent such as THF, ethylether, methanol, methanol/water and ethanol, or (2) with NaOMe, LiOH/H₂O₂, NaOH and so on at −20~50° C. for 30 min. ~1 day in a solvent such as methanol, ethanol, THF and methanol/water.

Compound (33) having the following general formula (33):

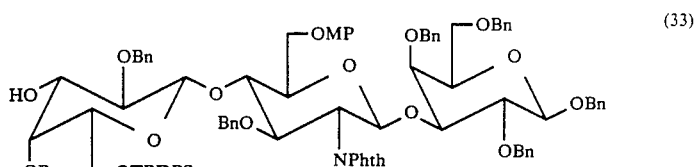

is produced by treating Compound (32) with an agent such as a general silylhalide, for example, TBDPS-Cl/imidazole, TBS-Cl and TMS-Cl, triethylamine, trimethylamine, lutidine, and pyridine at 0~70° C. for 1~40 hr. in a solvent such as DMF, ethylether, CH₂Cl₂, CHCl₃, CCl₄, pyridine, toluene and benzene.

Compound (34) having the following general formula (34):

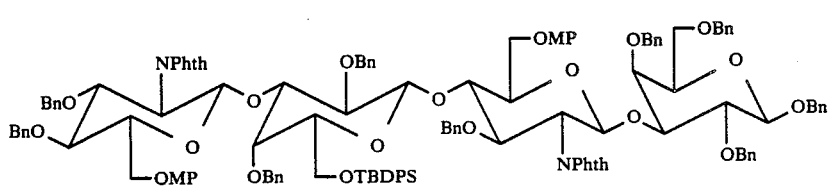

is produced by reacting Compound (33) with Compound (10) at −78~70° C. for 10 min.~1 day in the presence of a catalyst such as BF₃-OEt₂, TMS triflate, methyltriflate, SnCl₄ and TiCl₄ and in a solvent such as ClCH₂CH₂Cl, CH₂Cl₂, CHCl₃, CCl₄, nitromethane, ethylether, THF, toluene and benzene.

Compound (35) having the following general formula (35):

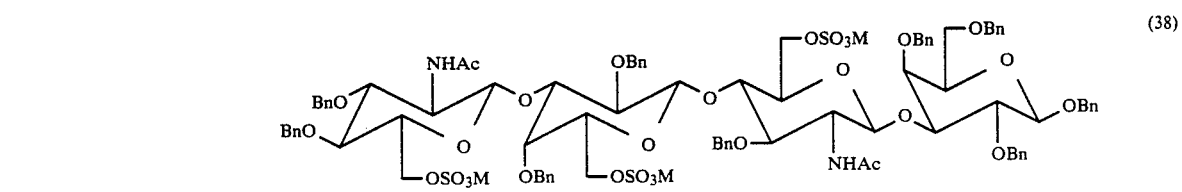

is produced by treating Compound (34) with an alkylamine such as NH₂NH₂.H₂O, n-BuNH₂ and EtNH₂ at 50° C.~a reflux temperature for 1 hr.~1 day in a solvent such as ethanol and methanol, and then by reacting the resulting compound with an acetylating agent such as Ac₂O and AcCl at 0~80° C. for 1~78 hr. in a solvent such as pyridine, methanol, triethylamine and DMAP.

Compound (36) having the following general formula (36):

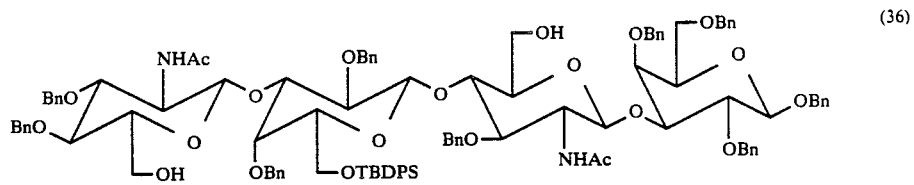

is produced by treating Compound (35) with CAN at −20~70° C. for 10 min.~1 day in a solvent such as CH₃CN/water, THF/water and dioxane/water.

Compound (37) having the following general formula (37):

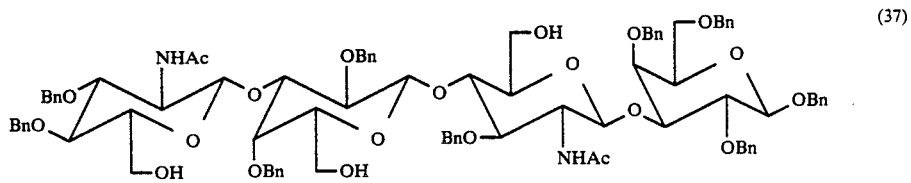

is produced by treating Compound (36) with n-Bu₄NF, HF, BF₃.OEt₂, KF/crown ether and the others of conventionally used fluoride compounds at −20~70° C. for 15 min.~1 day in a solvent such as THF, diethylether, CH₃CN and THF/water.

Compound (38) having the following general formula (38):

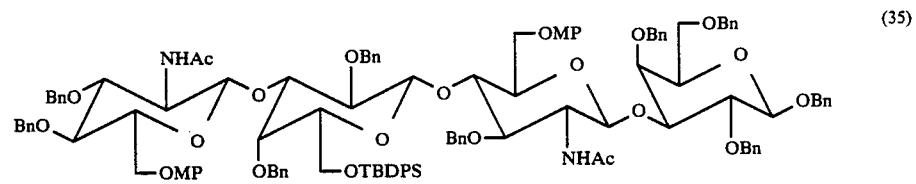

is produced by treating Compound (37) with SO₃.-NMe₃, SO₃.pyridine etc. at room temperature at 100° C. for 1~78 hr. in a solvent such as DMF and pyridine.

Incidentally, Compound (38) is treated with 10%-Pd/C, 5%-Pd/C, PtO₂, Pd(OH)₂, etc. at 0~80° C. for 1 hr. ~ 1 week in a solvent like methanol/water, methanol and CH₃OH/AcOH, to produce Compound (39) having the following general formula (39):

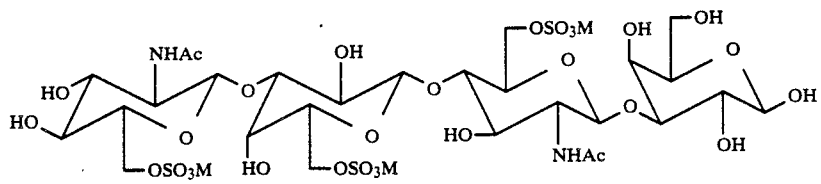

Compound (41) having the following general formula (41):

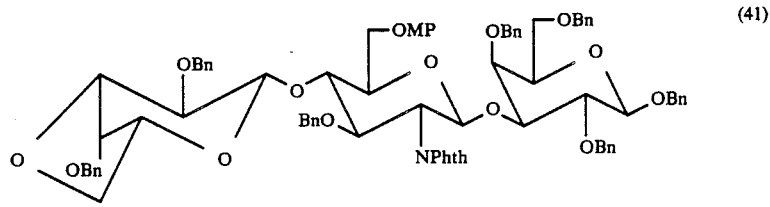

is produced by treating Compound (32) with

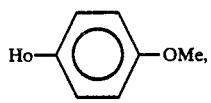

a phosphine such as triphenyl phosphine, tritoluoyl phosphine, tributyl phosphine, triethyl phosphine, EtOOCH=NCOOEt, etc. at $-20 \sim 80°$ C. for $1 \sim 40$ hr. in a solvent such as $CH_2Cl_2$, $CHCl_3CCl_4$ and $ClCH_2CH_2Cl$.

EXAMPLE

The following examples will further illustrate the present invention, but are not intended to limit it in any way.

Incidentally, the numbers of the compounds used in the following examples are the same as those of the compounds as stated in the above.

EXAMPLE 1

Production of Compound (7)

Dry p-methoxyphenol (76.59 g: 60.9 mmol), triphenyl phosphine (15.99 g: 60.9 mmol) and Compound (6) (13.4 g: 30.5 mmol) were dissolved in dichloromethane (200 ml) and then the solution was cooled at 0° C. under argon atmosphere. Diethylazodicarboylate (10.62 g: 60.9 mmol) was added to the solution, which was stirred at 0° C.~room temperature for 18 hr. The reaction mixture was poured into ice-water (500 ml) and washed. The water phase was extracted with dichloromethane (150 ml) and mixed with the organic phase. The mixture was washed with saturated aqueous NaCl solution (150 ml) and dried over anhydrous magnesium sulfate. Then, the solvent was removed under reduced pressure. The residue was purified by silica gel column chromatography (n-hexane:AcOEt=2:1 and PhCH₃:AcOEt=5:1), to produce Compound (7) (15.5 g: 93%).

Physical Properties of Compound (7)

$[\alpha]_D^{25}+21.8°$(C 1.03, CHCl₃),
Rf 0.34 (PhCH₃:AcOEt=3:1),

Elemental analysis: Found: C, 47.40; H, 5.92; N, 2.50, Calc.: $C_{31}H_{31}NO_8 \cdot \frac{1}{2}H_2O$; C, 67.14' H, 4.82; N, 2.53.

¹H-NMR (CDCl₃)δ; 2.555 (d, 1H: J−3.4 Hz; 4-OH), 3.784 (ddd; 1H; J₅₆=3.7 Hz, J₅₆−4.9 Hz, J₄₅=9.8 Hz; H-5), 3.892 (ddd; 1H; J₄.ₒₕ=3.1 Hz, J₃.₄=8.2 Hz; J₄₅=9.8 Hz; H-4), 4.245 (dd; 1H; J=8.2 Hz, J=10.7 Hz, H-2 or 3), 4.307 (dd; 1H; J=8.2 Hz, J=10.7 Hz, H-2 or 3), 4.229 (dd; 1H; J₄₅=5.2 Hz, J₆₆'=10.4 Hz; H-6), 4.275 (dd; 1H; J₅₆'=3.4 Hz; J₆₆'=10.1 Hz' H-6'), 4.554, 4.701 (2d; J=12.2 Hz, OCH₂Ph), 3.772 (s, 3H, OMe), 4.227 (dddd; Jad'=1.5 Hz; Jed'=1.5 Hz; Jcd'=4.9 Hz; Jdd'=12.8 Hz; Hd), 3.995 (ddd; Jad−1.4 Hz; Jed=1.4 Hz; Jcd=6.3 Hz; Jdd'=13.0 Hz; Hd), 5.667 (dddd; Jac=17.1 Hz; Jbc−10.6 Hz; Jcd=6.3 Hz; Jcd'=5.1 Hz; Hc), 5.007 (dddd; Jab=1.4 Hz; Jbd=1.4 Hz; Jbd'=1.4 Hz; Jbc=10.4 Hz; Hb), 5.086 (dddd; Jab=1.7 Hz; Jad=1.7 Hz; Jad'=1.7 Hz; Jac=17.2 Hz; Ha).

EXAMPLE 2

Production of Compound (8)

Ag₂O (13.5150 g: 58.3 mmol), benzyl bromide (10.1415 g: 59.3 mmol) and KI (3.3970 g: 23.7 mmol) were added to a solution of Compound (7) (5.3917:9.88 mmol) in DMF (150 ml) at 0° C. After being stirred at 0° C. to room temperature for 4 hr., the reaction mixture was poured into ethylether (350 ml), and then filtered through Celite. The filtrate was washed with water (300 ml). The water phase was extracted with ether (350 ml). The combined organic phase was washed with saturated aqueous NaCl solution (300 ml) and dried over anhydrous magnesium sulfate. After the solvent was evaporated, the residue was purified by silica gel column chromatography (n-hexane:AcO-Et=2:1), to produce Compound (8) (6.2028 g: 99%).

Physical Properties of Compound (8)

m.p. 54~55° C.
$[\alpha]_D^{25}+50.0°$(C 0.4, CHCl₃), Rf: 0.65 (n-hexane:AcOEt=1:2).

Elemental analysis: Found: C, 71.25; H; 5.85; N, 2,16, Calc.: (the compound is regarded as being defined by $C_{38}C_{37}O_8N \cdot 1/6\ H_2O$) C, 71.46; H, 6.15; N, 2,19, ¹H-NMR (CDCl₃)δ; 3.771 (s, 3H, -OMe), 3.7507~3.7830 (m, 1H, H-5), 3.8984 (dd, J=8.74, J=10.73, H-4), 3.974 (ddd, allyl H-d', 1H, Jbd'=1.15, Jad'=1.24, Jcd=6.27, Jdd=13.2 Hz), 4.128 (dd; 1H; J=4.41, J=10.40; H-6), 4.252 (dd; J=8.42, J=10.73H-2), 4.402 (dd, 1H, J=8.58, J=10.56; H-3), 4.4537, 4.8065 (2d: J=12.21, 2H, OCH$_2$Ph), 4.6284, 4.8672 (2d: J=10.89, 2H, OCH$_2$), 4.986 (dd, J=10.39 Hz; 1H; allyl.Hb), 5.068 (ddd, 1H; J=1.54, J=3.06, J=17.31 Hz; allyl Ha), 5.655 (m, 1H, allyl.Hc), 5.210 (d, J=8.25 Hz; H-1 1H).

EXAMPLE 3

Production of Compound (9)

A solution of Compound (8) (3.0 g: 4.72 mmol) in EtOH-PhH-H$_2$O (7:3:1 and 250 ml) was refluxed for 1 hr. under argon atmosphere. After cooling of the solution to the room temperature, RhCl(PPh$_3$)$_3$ (174.7 mg: 0.188 mmol) and DABCO (63.4 mg: 0.562 mmol) were added to the solution, which was refluxed for 4 hr. Further, RhCl(PPh$_3$)$_3$ (173.9 mg: 0.188 mmol) and DABCO (64.1 mg: 0.571 mmol) were added to the solution, which was refluxed for 4.5 hr. After the solvent was evaporated, HgO (433.2 mg: 2.00 mmol) and HgCl$_2$ (10.2660 g: 47.2 mmol) were added to the residue in acetone-H$_2$O (9:1, 210 ml). After being stirred at room temperature for 2.5 hr., the reaction mixture was poured into chloroform (1.0 l), and washed with water (1.0 l). The water phase was extracted with chloroform (500 ml). The combined organic phase was successively washed with 10% KI solution (500 ml) and saturated aqueous NaCl solution (500 ml), and dried over anhydrous magnesium sulfate. The solvent was distilled off under reduced pressure. The residue was purified by silica gel column chromatography (n-hexane:AcOEt=1:1), to produce Compound (9) (1.7350 g: 62%).

Physical Properties of Compound (9)

($\alpha$:$\beta$=1:3).
m.p. 176~178° C.
[$\alpha$]$_D^{21}$+87.1° (C 0.55, CHCl$_3$).
Rf=0.26 (n-hexane:AcOEt=1:1). Elemental Analysis: Found: C, 70.45; H, 5.60; N, 2.35. Calc.: (the compound is regarded as being defined by C$_{35}$H$_{33}$O$_8$N) C, 70.58; H, 5.58; N, 2.35.
$^1$H-NMR (CDCl$_3$)$\delta$; 3.7397 (s, 3H, OMe), 3.7549 (s, 3H, OMe), 3.8351 (ddd, J=1.983 Hz, J=4.27 Hz, J=9.91 Hz; 1H, H-5), 3.8824 (t, J=9.16 Hz, 1H, H-4), 4.0694 (dd, J$_{56}$'=4.27 Hz, J$_{66}$'=10.07 Hz; 1H, H-6'), 4.1661 (dd; J$_{56}$=1.83 Hz, J$_{66}$'=10.37 Hz; 1H, H-6), 4.1652 (dd, J=8.55 Hz, J=10.69 Hz; 1H; H-2 or 3), 4.4477 (dd; J=8.70 Hz, J=10.53 Hz; 1H; H-2 or 3), 4.4588, 4.8082 (2d, J=12.20 Hz, 2H, OCH$_2$Ph), 4.6163, 4.8594 (2D, J=10.99 Hz, 2H, OCH$_2$Ph), 4.6163, 4.8594 (2d, J=10.99 Hz, 2H, OCH$_2$Ph), 5.3736 (t, J=3.7 Hz, H-1$\alpha$), 5.4438 (t, J=8.09 Hz; H-1$\beta$).

EXAMPLE 4

Production of Compound (10) (X is Cl)

Trichloroacetonitrile (848.4 mg: 5.88 mmol) and DBU (12.8 mg: 0.084 mmol) were added to a solution of Compound (9) (91.0 mg: 0.153 mmol) in dichloromethane (2 ml) at 0° C. After being stirred at 0° C. for 2 hr., the reaction mixture was layered onto the top of silica gel column and chromatographed with a mixture of n-hexane and AcOEt (2:1), to produce Compound (10) (110.5 mg: 99%).

Physical Properties of Compound (10)

State: Transparent and Oily
[$\alpha$]$_D^{22}$=+73.7° (C 0.83, CHCl$_3$),
Rf: 0.45 (n-hexane:AcOEt=1:1),
$^1$H-NMR (CDCl$_3$)$\delta$; 3.7619 (s, 3H; OMe), 3.9576 (ddd; 1H; J$_{56}$'=1.94 Hz; J$_{56}$=3.56 Hz; J$_{45}$=9.87 Hz; H-5), 4.0618 (t; 1H; J=9.22 Hz; H-4), 4.2012 (dd; 1H; J$_{56}$=3.56, J$_{66}$'=10.68 Hz; H-6), 4.2624 (dd; 1H, J$_{56}$'=1.94 Hz; J$_{66}$'=10.68 Hz; H-6'), 4.5006, 4.8452 (2d; 2H, J=12.30 Hz; OCH$_2$Ph 2H), 4.6785, 4.8932 (2d; 2H, J=10.85 Hz, OCH$_2$Ph), 6.4530 (d, 1H, J=8.74 Hz; H-1), 8.5538 (S, 1H; C=NH).

EXAMPLE 5

Production of Compound (12)

A solution of Compound (10) (X=Cl) (253.5 mg: 0.348 mmol) in 1,2-dichloroethane (8 ml) and a solution of BF$_3$.OEt$_2$ (0.40 mmol) in 1,2-dichloroethane (2 ml) were, in this order, added to a mixture in 1,2-dichloroethane of Compound (11) (237.7 mg: 0.439 mmol) and molecular sieves 4A (1.5830 g) at −50° C. After the resultant mixture was stirred at −30~−40° C. for 2 hr., it was filtered through Celite. The filtrate was diluted with AcOEt (40 ml) and washed with a 1%-NaHCO$_3$ (40 ml). The water phase was extracted with AcOEt (40 ml). The organic phase was mixed with the water phase. The resultant mixture was washed with a saturated aqueous NaCl solution (40 ml) and dried with anhydrous magnesium sulfate. After the solvent was evaporated, the residue was purified by silica gel column chromatography (PhCH$_3$: AcOEt=15:1), to produce Compound (12) (287.0 mg: 76%) transparent and oily state).

Physical Properties of Compound (12)

[$\alpha$]$_D^{20}$=+4.9° (C 0.39, CHCl$_3$).
Rf: 0.60 (n-hexane:AcOEt=1:1). Elemental Analysis: Found: C, 72.76; H, 5.92; N, 1.39. Calc.: (the compound is regarded as being defined by C$_{69}$H$_{67}$O$_{13}$N.H$_2$O). C, 72.93; H, 4.94; N, 1.23
$^1$H-NMR (CDCl$_3$)$\delta$; 3.2889~3.5086 (m, 3H, H-5a, H-6a, H-6' a), 3.5604 (dd; 1H; J$_{1,2}$=7.59 Hz; J$_{2,3}$=9.90 Hz, H-2a), 3.7041 (dd; 1H, J$_{3,4}$=2.97 Hz; J$_{2,3}$=9.90 Hz, H-3a), 3.7605 (s; 3H, OMe) 3.7401~3.7493 (H-5), 3.9086 ($\alpha$; 1H; J$_{3,4}$=2.97 Hz; H-4a), 3.9353 (t; 1H; J=9.41 Hz=H-4b), 4.0940 (dd; 1H; J$_{56}$=4.45 Hz, J$_{66}$'=10.40 Hz; H-6b), 4.1979 (dd; 1H; J$_{45}$'=1.65 Hz; J$_{66}$'=10.23 Hz; H-6'b), 4.0453, 4.4844 (2d; 2H, J=11.38 Hz; OCH$_2$Ph), 4.2900, 4.3413 (2d; 2H; J=11.72 Hz; OCH$_2$Ph), 4.2910 (d; 1H; J=7.92 Hz; H-1a), 4.3179 (dd; 1H; J=8.42 Hz; J=10.72 Hz; H-2b), 4.4855 (dd; 1H; J=8.58 Hz; J=10.56 Hz; H-3b), 4.4414, 4.7657 (2d; 2H; J=12.21 Hz, OCH$_2$Ph), 4.4414, 4.8053 (2d; 2H; J=12.21 Hz, OCH$_2$Ph), 4.5301, 4.8861 (2d; 2H; J=11.88 Hz, OCH$_2$Ph), 4.6299, 4.8634 (2d; 2H; J=10.73 Hz, OCH$_2$Ph), 5.4901 (d; 1H; J=8.58 Hz; H-1b).

EXAMPLE 6

Production of Compound (13)

A solution of Compound (12) (103.3 mg: 0.0924 mmol) and NH$_2$NH$_2$.H$_2$O (1.5 ml: 29.0 mmol) in ethanol (4.5 ml) was refluxed for 2 hr. After the solvent was evaporated, the residue was dissolved in pyridine/acetic anhydride (1:1,3 ml), which was stirred at room temperature for 1 hr. After white precipitate was filtered off, the filtrate was azeotropically distilled using toluene, to remove the solvent. The residue was purified by silica gel chromatography (n-hexane:AcOEt =1:1), to produce Compound (13).

Physical Properties of Compound (13)

m.p. 149~150° C.

$[\alpha]_D^{20} = -14.1°$ (C 1.00, $CHCl_3$).

Rf: 0.59 (n-hexane:AcOEt=1:2) Elemental Analysis: Found: C, 73.36; H, 6.59; N, 1.39. Calc.: (the compound is regarded as being defined by $C_{63}H_{67}O_{12}N$) C, 73.45; H, 6.55; N, 1.36.

$^1$H-NMR ($CDCl_3$)δ; 1.4776 (s, 3H, NAc), 3.3536~3.5765 (m, 3H, H-5a, H-6a, H-6' a), 3.6936 (dd; $J_{24}$=2.97 Hz; $J_{2,3}$=9.90 Hz; H-2a), 3.7474 (s, 3H, OMe), 3.8720 (d, 1H; $J_{3,4}$=2.64 Hz; H-4a), 4.0534 (dd, 1H, $J_{56}$=4.79 Hz; $J_{66'}$=10.40 Hz; H-6b), 4.1520 (dd; 1H; $J_{56'}$=1.98 Hz; $J_{66'}$=10.28 Hz; H-6'b), 4.3465, 4.3929 (2d, 2H, J−11.88 Hz; $CH_2Ph$), 4.4063 (d, 1H, J=7.91, H-1a), 4.5953 (d, 1H, J=8.91, H-1b).

EXAMPLE 7

Production of Compound (14)

Ceric ammonium nitrate (CAN) (53.2 mg: 0.0971 mmol) was added to a solution of COmpound (13) (50.0 mg: 0.0485 mmol) in $CH_3CN$—$H_2O$ (9:1, 10 ml) at 0° C. After being stirred at 0° C. for 5 hr., CAN (26.6 mg: 0.0486 mmol) was further added to the mixture, which was stirred at 0° C. to room temperature for 1 hr. The mixture was poured into AcOEt (40 ml), and then washed with water (40 ml). The water phase was extracted with AcOEt (40 ml) and mixed with the organic phase. The mixture was washed with a saturated aqueous NaCl solution (40 ml) and dried with anhydrous magnesium sulfate. The solvent was evaporated and then the residue was purified by silica gel column chromatography (n-hexane:AcOEt=1:1), to produce Compound (14) (34.2 mg: 76%).

Physical Properties of Compound (14)

m.p. 96~98° C.

$[\alpha]_D^{20} = -17.7°$ (C 0.87, $CHCl_3$),

Rf: 0.43 (n-hexane:AcOEt=1:2),

Elemental Analysis: Found: C, 71.64; H, 6.54; N, 1.76. Calc.: (the compound is regarded as being defined by $C_{56}H_{61}O_{11}N.H_2O$) C, 71.39; H, 6.74; N, 1.49.

$^1$H-NMR ($CDCl_3$)δ; 1.5004 (s, 3H, NAc), 4.4203 (d, 1H, J=7.63 Hz'; H-1a), 4.4439, 4.4827 (2d; 2H; J=12.4 Hz, $OCH_2Ph$), 4.6820 (d, 1H, J=8.85 Hz; NH), (d, 1H, J=8.24 Hz; H-1b).

EXAMPLE 8

Production of Compound (15) (M=Na)

Sulfur trioxide trimethylamine complex ($SO_3$. $NMe_3$) (2.4 mg: 0.0169 mmol) was added to a solution of Compound (14) in DMF (0.2 ml). The resultant mixture was stirred at 50° C. for 22 hr. Then, $SO_3.NMe_3$ (2.4 mg: 0.0169 mmol) was further added to the mixture, which has stirred at 50° C. for 3 hr. The reaction mixture was diluted with chloroform-methanol (1:1, 3 ml), which was fed to Sephandex LH-20 and eluted with chloroform-methanol. The solvent was distilled off. The residue was dissolved in methanol-water and passed through Dowex-50 ($Na^+$) to be changed to its sodium salt form. The solvent was removed to produce Compound (15) (54. mg: 98%).

Physical Properties of Compound (15)

m.p. 221~223° C.

$[\alpha]_D = -15.2°$ (C 0.56, $CHCl_3$),

Rf: 0.71 ($CHCl_3$:MeOH=3:1).

Elemental Analysis: Found: C, 64.83; H, 6.04; N, 1.66. Calc.: (the compound is regarded as being defined by $C_{56}H_{60}O_{14}NSNa.\frac{1}{2}H_2O$) C, 64.98; H, 6.04; N, 1.35.

$^1$H-NMR ($CDCl_3$:MeOH=1:1)δ; 1.64071 (s, 3H, NAc), 3.8098 (dd, 1H, $J_{3,4}$=2.90 Hz; $J_{2,3}$=9.92 Hz; H-3a), 4.1500 (d, 1H, J=2.75 Hz; H-4a), 4.2961 (dd, $J_{56}$=4.58 Hz, $J_{66'}$=10.68 Hz; H-6b), 4.4402 (dd, $J_{56'}$=1.68 Hz, $J_{55'}$=10.84 Hz; H-6'b), 4.4612 (d, J=7.63, H-1a), 4.7800 (d, J=8.55, H-1b).

EXAMPLE 9

Production of Compound (16) (M=Na)

A solution of Compound (15) (5.4 mg: 0.00526 mmol) and 10%-Pd/c (5.7 mg) in a mixture of methanol and water (0.5 ml, 9:1) was stirred at room temperature for 24 hr. under hydrogen stream. Further, 10%-Pd/C (6.7 mg) was added to the resultant mixture and stirred at 50° C. for 42 hr. The reaction mixture was filtered and the filtrate was evaporated. The residue was purified using Sephadex G-10 and Biogel P-4 ($H_2O$), to produce Compound (16) (2.49 mg: 98%) (amorphous).

Physical Properties of Compound (16)

$[\alpha]_D^{22} = +10.5°$ (C 0.16, $H_2O$)

| Rf | 0.13 (n-BuOH:acetone:$H_2O$ = 6:5:1) |
|---|---|
| | 0.17 (n-BuOH:acetone:$H_2O$ = 6:5:1) |

$^1$H-NMR ($D_2O$) Standard:$Me_2C$=0) at 20° C. 2.003 (s; NAc), 4.5580 (d; J=8.25 Hz; H-1a β-anomer), 4.7015 (d; J=8.58 Hz; H-1b), 4.7226 (d; J=8.58 Hz; H-1b), 5.2220 (d; J−3.30 Hz; H-1a; α-anomer).

EXAMPLE 10

A solution of Compound (23) in 1,2-dichloroethane (10 ml) was added to a solution in 1,2-dichloroethane of Compound (7) (1.07 g: 1.99 mmol), silver triflate (1.023 g: 3.98 mmol) and molecular sieves 4A (6.0 g) at −10° C. under argon atmosphere. After being stirred at −10° C. to room temperature for 18 hr., the reaction mixture was filtered with Celite. The filtrate was diluted with ethyl acetate (50 ml), washed with sodium hydrogen carbonate aqueous solution (100 ml) and saturated aqueous NaCl solution (100 ml), and then dried over anhydrous magnesium sulfate. The solvent was evaporated and then the residue was purified by silica gel column chromatography (n-hexane: AcOEt=2:1), to produce Compound (24) (1.6 g: 92%). The α-anomer of Compound (24) was not produced.

Physical Properties of Compound (24)

m.p.=55~56° C.

$[\alpha]_D^{17} - +40.1°$ (C 0.92, $CHCl_3$).

Elemental Analysis: Found: C, 64.52; H, 6.26; N, 1.59, Calc.: (the compound is regarded as being defined by $C_{47}H_{53}O_{15}N$) C, 64.74; H, 6.13; N, 1.61.

Rf=0.22 (n-hexane:AcOEt=3:2).

$^1$H-NMR (500 MHz; $CDCl_3$)δ; 2.042 (s, 3H, Ac), 2.060 (s, 3H, Ac), 3.785 (s, 3H, OMe), 4.653, 4.678 (2d, J=12.3 Hz, $CH_2$), 4.537 (d, J=7.94, 1H, H-1b), 5.184 (d, J=8.55, 1H, H-1a), 5.380 (d, J=2.44 Hz, 1H, H-4b).

EXAMPLE 11

Production of Compound (25)

A 1.25N-LiOH (6 ml: 7.49 mmol) and a 31%-$H_2O_2$ (17 ml) were added to a solution of Compound (24)

(2.0836 g: 2.39 mmol) in THF (45 ml) at 0° C. After the mixture was stirred for 13 hr., the reaction mixture was diluted with ethyl acetate (100 ml) and washed with water (100 ml). The water phase was extracted with ethyl acetate (100 ml). The organic phase was added to the resultant water phase. Then, the mixture was washed with a saturated aqueous NaCl solution (100 ml) and dried over anhydrous magnesium sulfate. After the solvent was evaporated, the residue was purified by silica gel column chromatography (n-hexane:AcOEt−3:2), to produce purified Compound (25) (1.7133 g: 91%).

Physical Properties of Compound (25)

m.p. 55∼57° C.
$[\alpha]_D^{18} = +42.5°$ (C 1.25 CHCl$_3$).
Rf=0.39 (n-hexane:AcOEt=1:2).
Elemental Analysis: Found: C, 65.31; H, 6.32; N, 1.76. Calc.: (the Compound is regarded as being defined by $C_{43}H_{49}O_{13}N$) C, 65.55; H, 6.27; N, 1.78.

$^1$H-NMR (CDCl$_3$)δ; 3.7768 (s, 3H, OMe), 3.1219 (dd; 1H; J=3.05 Hz; J=9.46 Hz; H-3b), 3.6542 (dd; 1H; J=6.72 Hz; J=9.77 Hz), 4.2342 (dd; 1H; J=8.55 Hz; J=10.69 Hz), 4.3879 (dd; 1H; J=8.54 Hz; J=10.68 Hz), 4.4383 (d; 1H; J=7.94 Hz; H-1b), 4.4571, 4.8606 (2d; 2H; J=12.36 Hz; OCH$_2$Ph), 5.2013 (d; 1H; J=8.24 Hz; H-1a).

EXAMPLE 12

Production of Compound (26)

Ag$_2$O (3.4906 g: 15.06 mmol), benzyl bromide (1.9 ml: 15.58 mmol) and KI (1.0344 g: 6.23 mmol) were added to a solution of Compound (26) (1.0057 g: 1.28 mmol) in DMF (20 ml) at 0° C. After the mixture was stirred at 0° C. to room temperature for 5 hr., the reaction mixture was poured into ether (50 ml) and filtered through Celite. The fitrate was washed with water (50 ml). The water phase was extracted with either (50 ml). The organic phase was washed with saturated aqueous NaCl solution (50 ml) and dried over anhydrous magnesium sulfate. After the solvent was distilled off, the residue was purified by silica gel column chromatography (n-hexane:AcOEt=4:1), to produce Compound (26) (1.114 g:90%)

PHYSICAL PROPERTIES OF COMPOUND (26)

State: Transparent and Oily
$[\alpha]_D^{18} = +32.7°$ (C 0.49, CHCl$_3$).
Rf=0.37 (n-hexane:AcOEt=3:2). Elemental Analysis: Found: C, 70.47; H, 6.38; N, 1.44. Calc.: (the compound is regarded as being defined by $C_{57}H_{61}O_{13}N$) C, 70.72; H, 6.35; N, 1.45.

$^1$H-NMR (CDCl$_3$)δ; 3.1795 (dd; 1H; J=3.05 Hz; J=9.77 Hz; H-3b), 3.7165 (dd, 1H; J=7.93 Hz; J=9.77 Hz; H-2b), 3.7476 (s, 3H, OMe), 3.8001 (d; 1H; J=2.45 Hz; H-4b), 4.1479 (t; 1H; J=9.16 Hz; H-4a), 4.2565 (dd, 1H; J=8.24 Hz; J=10.68 Hz; H-2a), 4.3461 (d; 1H; J=7.93; H-1b), 4.7932, 4.8637 (2d; J=10.98 Hz; OCH$_2$Ph), 5.1970 (d, 1H; J=8.24 Hz; H-1a).

EXAMPLE 13

Production of Compounds (28) and (40)

A solution of Compound (26) (48.6 mg: 0.0502 mmol) in EtOH-PhH-H$_2$O (7:3:1, 2.8 ml) was refluxed for 1 hr. under argon stream. Then, RhCl (PPh$_3$)$_3$ (5.6 mg: 0.006 mmol) and DABCO (1.9 mg: 0.0180 mmol) were added to the solution, which was refluxed for 16 hr. The solvent was evaporated and the residue was dissolved in acetone-H$_2$O (10:1, 2.2 ml), to which HgO (4.6 mg: 0.0212 mmol) and HgCl$_2$ (138.6 mg: 0.673 mmol) were added. After the reaction mixture was stirred at room temperature for 1 hr., it was poured into chloroform (20 ml) an washed with water (20 ml). The water phase was extracted with chloroform (20 ml) and AcOEt (20 ml). The organic phase was added to the water phase and then the mixture was washed with a 10%-KI solution (20 ml) and then saturated aqueous NaCl solution (20 ml), and dried over anhydrous magnesium sulfate, which the solvent was distilled off under reduced pressure. The residue was dissolved in acetic anhydride-pyridine (1:2, 1.5 ml) and stirred at room temperature for 1 hr. in the presence of a catalytic amount of DMAP. The solvent was removed by azeotropic distillation with toluene, and the residue was purified by silica gel column chromatography (n-hexane:AcOEt=2:1), to produce Compound (28) (34.5 mg: 71%, α:β=1:11) and Compound (40) (11.5 mg: 24%).

Physical Properties of Compound (28)

(1) β-anomer
m.p. 153∼154° C.
$[\alpha]_D^{18} = +41.7°$ (C 0.39 CHCl$_3$),
Rf=0.26 (n-hexane:AcOEt=1:1).
Elemental Analysis: Found: C, 66.93; H, 5.71; N, 1.48. Calc.: (the compound is regarded as being defined by $C_{54}H_{55}O_{16}N$) C, 66.59; H, 6.59; N, 1.44.

$^1$H-NMR (CDCl$_3$)δ; 1.9281 (s, 3H, Ac), 1.9397 (s, 3H, Ac), 1.9934 (s, 3H, Ac), 3.7659 (s, 3H, OMe), 3.9410 (dd; 1H; J=7.33 Hz; J=10.99 Hz; H-2b), 4.0643 (dd; 1H; J=1.53 Hz; J=10.68 Hz; H-6'a), 4.1503 (dd; 1H; J=6.10 Hz; J=10.99 Hz; H-6a), 4.3687 (dd; 1H; J=8.85 Hz; J=10.68 Hz; H-2a), 4.4133 (d; 1H; J=7.93 Hz; H-1b), 4.4523 (dd; 1H; J=8.55 Hz; J=10.99 Hz; H-3a or 4a), 4.4613, 4.8673 (2d: 2H; J=12.21 Hz; OCH$_2$Ph), 4.4174, 4.5446 (2d: 2H; J=11.60 Hz; OCH$_2$Ph), 4.6537 (dd; 1H; J=3.21 Hz; J=10.23 Hz; H-3b), 6.3203 (d; 1H; J=8.85 Hz; H-1a).

(2) α-anomer
m.p. 55∼57° C.
$[\alpha]_D^{21} = +56.1°$ (C 1.5, CHCl$_3$),
Rf: 0.28 (n-hexane:AcOEt=1:1).
Elemental Analysis: Found: C, 66.13; H, 5.69, N, 1.44. Calc.: (the compound is regarded as being defined by $C_{54}H_{55}O_{16}N$) C, 66.59; H, 5.69; N, 1.44.

$^1$H-NMR (CDCl$_3$)δ; 1.9305 (s, 3H, Ac), 1.9507 (s, 3H, Ac), 2.0965 (s, 3H, Ac), 3.7726 (s, 3H, OMe), 3.9297 (dd; 1H; J=7.02 Hz; J=10.99 Hz; H-2b), 4.2839 (t; 1H; J=9.46 Hz; H-4a), 4.3388 (dd; 1H; J=2.75 Hz; J=10.68 Hz; H-6a), 4.4551 (d, 1H, J=7.63; H-1b), 4.5908 (dd; 1H; J=3.67 Hz; J=11.44 Hz; H-2a), 4.6918 (dd; 1H; J=3.05 Hz; J=10.07 Hz; H-3b), 5.0853 (dd; 1H; J=9.16 Hz; J=11.30 Hz), 6.2700 (d; 1H; J=3.66 Hz; H-1a).

Physical Properties of Compound (40)

State: transparent and Oily
$[\alpha]_D^{22} = +32.9°$ (C 0.37, CHCl$_3$).
Rf: 0.30 (n-hexane:AcOEt=1:1).
Elemental Analysis: Found: C, 67.54; H, 5.98, N, 1.51. Calc.: (the compound is regarded as being defined by $C_{55}H_{59}O_{15}N$) C, 67.82; H, 6.10; N, 1.44.

$^1$H-NMR (CDCl$_3$)δ; 1.0019 (t; 3H; J=7.17 Hz; CH$_2$CH$_2$CH$_3$), 1.9287 (s, 3H; Ac), 1.9855 (s, 3H; Ac), 3.4669 (dd; 1H; J=7.17 Hz; J=9.92 Hz), 3.6692 (ddd; 1H; J=1.83 Hz; J=3.74 Hz; J=9.92 Hz; H-5a), 3.9358 (dd; 1H; J=7.02 Hz; J=10.99 Hz), 4.1790 (dd; 1H;

J=8.85 Hz; J=10.07 Hz), 4.2171 (dd; 1H; J=8.55 Hz; J=10.69 Hz), 4.2586 (dd; 1H; J=3.66 Hz; J=10.37 Hz; H-3b), 4.3239 (dd; 1H; J=8.39 Hz; J=10.75 Hz), 4.5898 (d, 1H; J=7.63 Hz; H-1b), 5.1760 (d; 1H; J=8.53 Hz; H-1a).

EXAMPLE 14

Production of Compound (29)

A solution of Compound (28) (417.8 mg; 0.429 mmol) and $NH_2NH_2 \cdot AcOH$ (46.8 mg; 0.508 mmol) in DMF (5 ml) was heated at 50° C. for 10 min. $NH_2NH_2 \cdot AcOH$ (45.8 mg; 0.497 mmol) was further added to the solution and heated at 50° C. for 10 min. The reaction mixture was diluted with AcOEt (100 ml) and washed with a 10%-$NaHCO_3$ solution (100 ml). The water phase was extracted with AcOEt (100 ml). The organic phase was mixed with the water phase and washed with a saturated aqueous NaCl solution. The mixture was dried over anhydrous magnesium sulfate. The solvent was distilled off and the residue was purified by silica gel column chromatography (n-hexane:AcOEt=3:1), to produce Compound (29) (290.5 mg; 73%).

Physical Properties of Compound (29)

m.p. 73~75° C.
$[\alpha]_D^{22}= +49.3°$ (C 0.54, $CHCl_3$),

| Rf | 0.18 (n-hexane:AcOEt = 1:1) |
|---|---|
| | 0.23 (n-hexane:AcOEt = 1:1) |

Elemental Analysis: Found: C, 66.77; H, 5.75, N, 1.53. Calc.: (the compound is regarded as being defined by $C_{52}H_{53}O_{15}N$) C, 67.01; H, 5.73; N, 1.50.

$^1H$-NMR ($CDCl_3$)δ; 1.9427 (s, OAc (β-anomer)), 1.9311 (s, OAc (α-anomer)), 1.9659 (s, OAc (α-anomer)), 1.9787 (s, OAc (β-anomer)), 3.7537 (s, OME (β-anomer)), 3.7665 (s, OME (α-anomer)), 5.3776 (d; J=8.85 Hz, H-1a (β-anomer)).

EXAMPLE 15

Production of Compound (30) (X=Cl)

Trichloroacetonitrile (387.0 mg; 2.68 mmol) and DBU (8.0 mg; 0.053 mmol) were added to a solution of Compound (29) (100.1 mg; 0.107 mmol) in dichloromethane (2ml) at 0° C. After being stirred at 0° C. for 3.5 hr., the reaction mixture was fed into a silica gel column and eluted with n-hexane:AcOEt=2:1. The solvent was distilled off to produce Compound (30) (100.6 mg; 87%).

Physical Properties of Compound (30) (X=Cl)

State: Amorphous
$[\alpha]_D^{22}= +57.9°$ (C 0.45, $CHCl_3$).
Rf: 0.34 (n-hexane:AcOEt=1:1).
$^1H$-NMR ($CDCL_3$)δ; 1.9385 (s, 3H, Ac), 2.0019 (s, 3H, Ac), 3.7645 (s, 3H, OMe), 3.9469 (dd, 1H; J=6.97 Hz; J=11.17 Hz), 4.4723 (d; 1H; J=7.77 Hz; H-1b), 6.4426 (d; 1H; J=8.41 Hz; H-1a), 8.5351 (s, 1H; C=NH).

EXAMPLE 16

Production of Compound (31)

A solution of Compound (30) (2.02 mg: 1.88 mmol) in 1,2-dichloroethane (30 ml) and a solution of $BF_3 \cdot OEt_2$ (2.7 mmol) in 1,2-dichloroethane (10 ml) were added in this order to a solution in 1,2-dichloroethane (80 ml) of Compound (11) (1.8247 g: 3.38 mmol) and molecular sieves AW-300 (21.2304 g) at −25° to −30° C. After the mixture was stirred at −25~30°b C. for 2 hr., the reaction mixture was filtered through Celite. The filtrate was diluted with AcOEt (350 ml) and washed with 1%-$NaHCO_3$ (300 ml). The water phase was extracted with AcOEt (300 ml). The organic phase was mixed with the water phase. The mixture was washed with a saturated aqueous NaCl solution (300 ml) and dried over anhydrous magnesium sulfate. The solvent was distilled off and the residue was purified by silica gel column chromatography (n-hexane:AcOEt=3:1), to produce Compound (31) (2.2629 g: 83%),

Physical Properties of Compound (31)

$[\alpha]_D^{22}= +9.1°$ (C 0.67, $CHCl_3$).
Rf: 0.43 (n-hexane:AcOEt=1:1),
Elemental Analysis: Found: C, 71.17; H, 6.13; N, 1.04, Calc.: (the compound is regarded as being defined by $C_{86}H_{87}O_{20}N$) C, 71.01; H, 6.03; N, 0.96.

$^1H$-NMR ($CDCl_3$)δ; 1.9433 (s, 3H, Ac), 1.9543 (s, 3H, Ac), 3.2857 (dd; 1H; J=5.34 Hz; J=9.31 Hz; H-6b), 3.5685 (dd; 1H; J=7.79 Hz; J=9.62 Hz), 3.6884 (dd; 1H; J=3.06 Hz; J=9.77 Hz; H-6'b), 3.7476 (s, 3H, OMe), 3.7811 (dd; 1H; J=7.63 Hz; J=10.07 Hz), 3.8775 (d; 1H; J=2.44 Hz; H-4), 3.9184 (dd; 1H; J=7.33 Hz; J=10.99 Hz), 4.2922 (d; 1H; J=7.63 Hz; H-1c), 4.4416 (d; 1H; J=7.63 Hz; H-1a), 4.7055 (dd; 1H; J=3.67 Hz; J=9.77 Hz; H-3c), 5.4783 (d; 1H; J=8.24 Hz; H-1b).

EXAMPLE 17

Production of Compound (32)

(1) First Process 1.25N-LiOH (0.11 ml: 0.088 mmol) and 31%-$H_2O_2$ (0.40 ml) were added to a solution of Compound (31) (77.5 mg; 0.0533 mmol) in THF (1. 2 ml) at 0° C. After being stirred for 34 hr., the reaction mixture was diluted with ethyl acetate (40 ml) and washed with water (40 ml). The water phase was extracted with ethyl acetate (40 ml). The organic phase was mixed with the water phase. The mixture was washed with a saturated aqueous NaCl solution (40 ml) and dried over anhydrous magnesium sulfate. The solvent was evaporated and the residue was purified by silica gel column chromatography (n-hexane:AcOEt=2:1), to produce Compound (32) (66.0 mg; 90%).

(2) Second Process

A 0.1N-NaOMe/MeOH solution (3 ml; 0.3 mmol) was added to a methanol solution (10 ml) of Compound (31) (504.4 mg; 0.347 mmol) at 0° C. After being stirred at room temperature for 4.5 hr., Amberlyst-15 was added to the mixture. After the resin was removed, the solvent was distilled off. The residue was purified by silica gel column chromatography (n-hexane:AcOEt=1:1), to produce Compound (32) (378.4 mg; 80%).

Physical Properties of Compound (32)

State: Transparent and Oily
$[\alpha]_D^{20}= -3.7°$ (C 0.62, $CHCl_3$).
Rf: 0.49 (n-hexane:AcOEt=1:2)
Elemental Analysis: Found: (First Process) C, 70.56; H, 6.03; N, 1.08. (Second Process) C, 71.42; H, 5.11; N, 0.99. Calc.: (the compound is regarded as being defined by $C_{82}H_{83}O_{18}N \cdot H_2O$) C, 70.92; H, 6.17; N, 1.01 (the compound is regarded as being defined by $C_{82}H_{83}O_{18}N$) C, 71.86; H, 6.10; N, 1.02.

$^1H$-NMR ($CDCL_3$)δ; 3.7421 (s, 3H, OMe), 3.6295 (d; 1H; J=3.36 Hz; H-4), 3.7030 (dd; 1H; J=3.05 Hz;

J=9.77 Hz; H-6'b), 3.8782 (d; 1H; J=2.44 Hz; H-4), 4.2421 (dd; 1H; J=3.82 Hz; J=10.53 Hz; H-3), 4.2976 (d; 1H; J=7.63 Hz; H-1c), 4.3483 (d; 1H; J=7.63 Hz; H-1a), 5.4996 (d; 1H; J=8.24 Hz; H-1b), $^{13}$C-NMR (CDCl$_3$)δ; 99.68 (d; J=166.0 Hz; C-1), 102.57 (d; J=157.0 Hz; C-1), 103.30 (d; J=160.0 Hz; C-1).

EXAMPLE 18

Production of Compound (33)

A solution of Compound (32) (378.4 mg; 0.274 mmol) in DMF (5 ml) was added to a solution in DMF (5 ml) of TBDPSCl (0.11 ml; 0.414 mmol) and imidazole (32.0 mg; 0.469 mmol). After being stirred at room temperature for 24.5 hr., the reaction mixture was poured into ether (200 ml) and washed with water. The water phase was extracted with ether (200 ml×2). The organic phase was mixed with the water phase. The mixture was washed with a saturated aqueous NaCl solution and dried over anhydrous magnesium sulfate. The solvent was evaporated and the residue was purified by silica gel column chromatography (n-hexane:AcOEt=8:3), to produce Compound (33) (344.4 mg; 78%).

Physical Properties of Compound (33)

State: Transparent and Oily
$[\alpha]_D^{22}=-0.2$ (C 1.1, CHCl$_3$).
Rf: 0.65 (n-hexane:AcOEt=1:2).
Elemental Analysis: Found: C, 72.45; H, 6.31; N, 0.79. Calc.: (the compound is regarded as being defined by $C_{98}H_{101}O_{18}NSI.H_2O$) C, 72.35; H, 6.39; N, 0.86.

$^1$H-NMR (CDCl$_3$)δ; 1.0184 (s, 9H, t-Bu), 3.2637 (dd; 1H; J=5.19 Hz; J=9.46 Hz; H-6b), 3.2976 (t; 1H; J=7.48 Hz), 3.5587 (dd; 1H; J=7.63 Hz; J=9.77 Hz), 3.6750 (dd; 1H; J=3.05 Hz; J=9.76 Hz; H-6'b), 3.7573 (s, 3H, OMe), 3.8611 (d; 1H; J=2.44 Hz; H-4), 3.9444 (d; 1H, J=3.05 Hz; H-4), 4.2860 (d; 1H; J=7.63 Hz; H-1a or c), 4.2931 (d; 1H, J=7.33 Hz; H-1a or c), 4.4536 (d; 1H, J=8.54 Hz; H-1b).

EXAMPLE 19

Production of Compound (34)

A solution of Compound (10) in 1,2-dichloroethane (10 ml) and BF$_3$.OEt$_2$ (0.10 mmol) were added in this order to a solution in 1,2-dichloroethane (10 ml) of Compound (33) (344.4 mg; 0.214 mmol) and molecular sieves AW-300 (2.0566 g) at −23° C. under argon stream. After the stirring was continued at −23° to −25° C. for 1.5 hr., the reaction mixture was filtered by Celite. The filtrate was diluted with AcOEt (200 ml) and washed with 1%-NaHCO$_3$ (200 ml). The water phase was extracted with AcOEt (200 ml). The organic phase was mixed with the water phase. The mixture was washed with a saturated aqueous NaCl solution (150 ml) and dried over anhydrous magnesium sulfate. The solvent was evaporated and the residue was purified by silica gel column chromatography (PhCH$_3$:AcOEt=15:1) and PLC (PhCH$_3$:AcOEt=7:1), to produce Compound (34) (225.0 mg; 48%). Also, 33% of Compound (33) was recovered. By taking the recovered Compound (33) into consideration, the yield of Compound (34) was 72%.

Physical Properties of Compound (34)

State: Transparent and Oily
$[\alpha]_D^{22}=-4.4°$ (C 0.94, CHCl$_3$),
Rf: 0.57 (PhCH$_3$:AcOEt=5:1).
Elemental Analysis: Found: C. 71.82; H, 5.89, N, 1.34, Calc.: (the compound is regarded as being defined by $C_{133}H_{132}O_{25}N_2Si.2H_2O$) C, 71.87; H, 6.17; N, 1.26, $^1$H-NMR (CDCl$_3$)δ; 0.8384 (s, 9H, t-Bu), 3.7037 (s, 3H, OMe), 3.7885 (s, 3H, OMe), 4.1707 (d; 1H; J=7.63; H-1a or c), 4.22717 (d; 1H; J=7.32; H-1a or c), 5.2660 (d; 1H; J=8.24; Hz; H-1d), 5.43496 (d; 1H; J=8.24; Hz; H-1b), $^{13}$C-NMR (CDCl$_3$)δ; 99.25 (d, J=162.0 Hz; C-1), 99.82 (d, J=166.0 Hz; C-1), 102.55 (d, J=156.5 Hz; C-1), 102.93 (d, J=159.0 Hz; C-1),

EXAMPLE 20

Production of Compound (35)

A solution in ethanol (10 ml) of Compound (34) (107.2 mg; 0.0529 mmol) and NH$_2$NH$_2$.H$_2$O (1.54 ml; 37.1 mmol) was refluxed for 3 hr. The solvent was evaporated. The residue was dissolved in pyridine-acetic anhydride (1:1; 6 ml) and stirred for 23 hr. The solvent was removed by azeotropic distillation with toluene. The residue was purified by silica gel column chromatography (PhCH$_3$:AcOEt=10:1 and 3:1), to produce Compound (35) (62.3 mg; 63%).

Physical Properties of Compound (35)

$[\alpha]_D^{22}=-6.4°$ (c 0.33, CHCl$_3$),
Rf: 0.78 (PhCH$_3$:acetone=3:1).
Elemental Analysis: Found: C, 71.85; H, 6.70; N, 1.22. Calc.: (the compound is regarded as being defined by $C_{121}H_{132}O_{23}N_2Si$) C, 72.29; H, 6.62; N, 1.39.

$^1$H-NMR (CDCl$_3$)δ; 0.8835 (s, 9H, t-Bu), 1.3820 (s, 9H, NAc), 1.4375 (s, 9H, NAc), 3.7146 (s, 9H, OMe), 3.7372 (s, 9H, OMe), 4.3645 (d; J=7.33; H-1a), $^{13}$C-NMR (CDCl$_3$)δ; 101.67 (d, J=161.02; C-1), 101.77 (d, J=161.02; C-1), 102.63 (d, J=158.49; C-1), 103.16 (d, J=165.23; C-1).

EXAMPLE 21

Production of Compound (36)

Ceric ammonium nitrate (CAN) (40.0 mg; 0;.0730 mmol) was added to a solution of Compound (35) (21.9 mg; 0.0109 mmol) in CH$_3$CH—H$_2$O (9:1; 3 ml) at 0° C. After the stirring was continued at 0° C. for 1.5 hr., the reaction mixture was poured into AcOEt (20 ml) and washed with water (20 ml). The water phase was extracted with AcOEt (20 ml×2). The organic phase was mixed with the water phase. The mixture was washed with a saturated common salt aqueous solution (10 ml) and then dried over anhydrous magnesium sulfate. The solvent was evaporated and the residue was purified by silica gel column chromatography (PhCH$_3$: acetone 3:1), to produce Compound (36) (14.9 mg; 75%).

Physical Properties of Compound (36)

State: Transparent and Oily
$[\alpha]_D^{21}=-19.2°$ (C 0.74; CHCl$_3$).
Rf: 0.36 (PhCH$_3$:Acetone=3:1).
Elemental Analysis: Found: C, 70.01; H, 6.74; N, 1.46. Calc.: (the compound is regarded as being defined by $C_{107}H_{120}O_{21}N_2SI.2H_2O$) C, 70.06: H, 6.70; N, 1.52.

$^1$H-NMR (CDCl$_3$)δ; 1.0165 (s, 9H), t-Bu), 1.4314 (s, 3H), NAc), 1.4662 (s, 3H), NAc), 4.3806 (d, 1H, J=7.63 Hz; H-1a), 4.6106 (d, 1H, J=8.24 Hz; H-1),

EXAMPLE 22

Production of Compound (37)

A solution of 1.0 M Bu₄NF in THF (0.07 ml; 0.07 mmol) was added to a solution of Compound (36) (20.8 mg; 0.0115 mmol) in THF (2 ml) at 0° C. under argon stream. After being stirred at 0° C. to room temperature for 3 hr., the reaction mixture was diluted by toluene (10 ml). The solvent was evaporated at 40° C. The residue was dissolved in AcOEt (20 ml) and washed with water (10 ml). The water phase was extracted with AcOEt (20 ml×2). The organic phase was mixed with the water phase. The mixture was washed with a saturated aqueous NaCl solution (10 ml) and dried with anhydrous magnesium sulfate. The solvent was evaporated. The residue was purified by silica gel column chromatography (PhCH₃:acetone=5:4), to produce Compound (37) (14.0 mg; 78%).

Physical Properties of Compound (36)

State: Amorphous
$[\alpha]_D^{21} = -17.3°$ (C 0.37; CHCl₃).
Rf: 0.32 (PhCH₃:acetone−1:1).
Elemental Analysis: Found: C, 69.12; H, 6.78; N, 1.62. Calc.: (the compound is regarded as being defined by $C_{91}H_{102}O_{21}N_2 \cdot H_2O$) C, 69.27; H, 6.64; N, 1.78.
¹H-NMR (CDCl₃)δ; 1.4735 (s, 3H, NAc), 1.5059 (s, 3H, NAc), 4.3934 (d, 1H, J=7.63 Hz, H-1a), ¹³C-NMR (CDCl₃:methanol-d₄=1:1)δ; 101.76 (C-1), 102.09 (C-1×2), 102.17 (C-1).

EXAMPLE 23

Production of Compound (38) (X=Na)

Sulfur trioxide trimethyl amine complex (SO₃.NMe₃) (17.5 mg; 0.126 mmol) was added to a solution of Compound (37) (15.2 mg; 0.00974 mmol) in DMF (0.5 ml), which was stirred at 65~75° C. for 19.5 hr. The reaction mixture was diluted with chloroform-methanol (1:1, 3 ml), fed into sephadex LH-20, and eluted with chloroform-methanol (1:1). The solvent was distilled off. The residue was dissolved in methanol and passed through Dowex-50 (Na³⁰) to be changed to its sodium salt. The solvent was distilled off, to produce Compound (38) (17.8 mg; 98%).

Physical Properties of Compound (38)

State: Amorphous
$[\alpha]_D^{22} = -10.5°$ (C 1.19, CHCl₃),
Rf: 0.27 (CHCl₃:MeOH=3:1).
Elemental Analysis: Found: C. 55.99; H, 5.68; N, 1.94, Calc.: (the compound is regarded as being defined by $C_{91}H_{99}O_{30}N_2S_3Na_3 \cdot 5H_2O$) C, 55.88; H, 5.62; N, 1.44.
¹³C-NMR (CDCl₃: MeOH-d₄), 100.8695 (C-1), 101.8280 (C-1), 102.0224 (C-1), 102.5788 (C-1), 171.1187 (NAc), 171.2193 (NAc), 22.2412 (NAc), 22.3552 (NAc).

EXAMPLE 24

Production of Compound (39)

A solution in methanol-water ((9:1; .5 ml) of Compound (38) (2.5 mg; 0.00134 mmol) and 10%-Pd/C (3.1 mg) was stirred at room temperature for 21 hr. under hydrogen stream. The reaction mixture was filtered. The filtrate was evaporated and the residue was purified by Sephadex G-10 (H₂O). By freeze-drying, water was removed, to produce Compound (39) (1.3 mg; 92%).

Physical Properties of Compound (39)

$[\alpha]_C^{22} = +11.9°$ (C 0.009, H₂O).
Rf: 0.50 (n-BuOH: acetone:H₂O=6:5:4).
¹H-NMR(D₂O)δ_H (standard acetone δ=2.225); 4.5309 (d, J=8.06 Hz; H-1c), 4.5342 (d, J=7.69 Hz; H-1c), 4.5609 (d, J=8.06 Hz; H-1a (β-anomer)), 5.2263 (d, J=3.30 Hz; H-1a (α-anomer)), 2.0324 (s, NAc), 2.0433 (s, NAc), ¹³C-NMR (D₂O)δ(standard acetone δ=30.3 ppm); 102.65, 102.86, 102.98, 103.03.

EXAMPLE 25

Production of Compound (41)

Dried p-methoxyphenol (37.3 mg; 0.298 mmol), triphenyl phosphine (78.7 mg; 0.298 mmol) and Compound (32) (136.2 mg; 0.0994 mmol) were dissolved in dichloromethane (5 ml) and cooled at 0° C. under argon stream. A solution of diethyazocarboxylate (52.8 mg; 0.298 mmol) in dichloromethane (1.5 ml) was dropwise added to the resulting solution. After the stirring was continued at 0° C. to room temperature for 21 hr., the reaction mixture was poured into dichloromethane (50 ml) and fully washed with ice-water (50 ml). The water phase was extracted with dichloromethane (50ml). The organic phase was mixed with the water. The mixture was washed with a saturated aqueous NaCl solution (50 ml) and dried over anhydrous magnesium sulfate. The solvent was removed under reduced pressure. The residue was purified by silica gel column chromatography (n-hexane:AcOEt=1:1), to produce Compound (41) (134.7 mg; 100%).

Physical Properties of Compound (41)

m.p. 40~41° C.
$[\alpha]_D^{17} = -17.4°$ (C 1.03, CHCl₃),
Rf: 0.43 (n-hexane:AcOEt−1:1),
¹H-NMR (CDCl₃); δ; 4.2967 (d, 1H, J=7.94 Hz; H-1), 4.4245 (d, 1H, J=7.63 Hz; H-1), 5.4777 (d, 1H, J=8.24 Hz; H-1), ¹³C-NMR(CDCl₃): δ; 99.69 (d, J=166.0 Hz; H-1), 101.25 (d, J=166.0 Hz; H-1), 102.60 (d, J=158.0 Hz; H-1),

What is claimed is:

1. Sulfated oligosaccharides or their derivatives having the following formula:

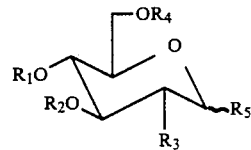

wherein (1) R₁=R₂=C₆H₅CH₂ (Bn),

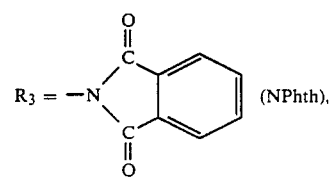

(NPhth),

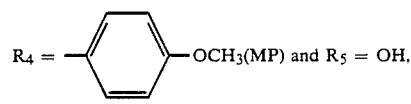

R₄ = —⟨phenyl⟩—OCH₃(MP) and R₅ = OH,

-continued (wherein X = a halogen atom) or

[structure: sugar ring with OBn groups]

② R₁ = R₂ = Bn, R₃ = NHAc (Ac = an acetyl group), R₄ = H, MP or SO₃M (wherein M = an alkali metal) and R₅ = [sugar structure with OBn groups], ③ R₁ = [sugar structure with allyl ether groups, OR₆]

(wherein R₆ = Ac, Bn or H), R₂ = Bn, R₃ = NPhth, R₄ = MP and R₅ =

[allyl ether structure],

④ R₁ = [sugar structure with HO, OBn, OH],

R₂ = Bn, R₃ = NPhth, R₄ = MP and R₅ = OH.

⑤ R₁ = [sugar structure with AcO, OBn, OAc],

R₂ = Bn, R₃ = NPhth, R₄ = MP and R₅ = OAc, OH,

[two structures with O-propyl and O-C(=NH)CX₃]

(X is a halogen atom) or

[sugar structure with OBn groups],

⑥ R₁ = [sugar structure with HO, OBn, OR₇]

[wherein R₇ = H or t-Bu(C₆H₅)₂Si-(TBDPS)] R₂ = Bn, R₃ = NPhth, R₄ = MP and

R₅ = [sugar structure with OBn groups],

⑦ R₁ = [disaccharide structure with R³, BnO, OMP, OBn, OTBDPS]

R₂ = Bn, R₃ = NPhth or NHAc, R₄ = MP and

R₅ = [sugar structure with OBn groups],

⑧ R₁ = [disaccharide structure with NHAc, BnO, OH, OBn, OR₈]

(wherein R₈ = H or TBDPS), R₂ = Bn, R₃ = NHAc, R₄ = H and

R₅ = [sugar structure with OBn groups]

⑨ 
$R_1 =$ 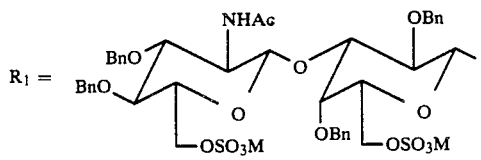
(wherein M=an alkali metal), $R_2$=Bn, $R_3$=NHAc, $R_4$=SO$_3$M and
$R_5 =$ 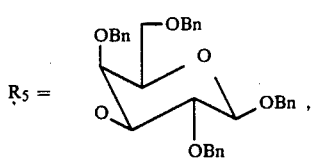
and
⑩
$R_1 = O$ 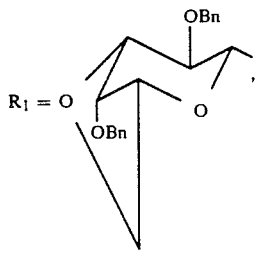
$R_2$=Bn, $R_3$=NPhth, $R_4$=MP and
$R_5 =$ 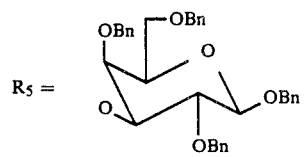
2. A pure form of a sulfated oligosaccharide having the following formula:
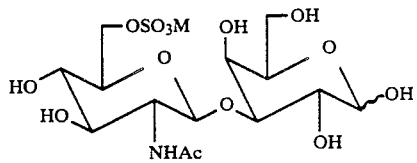
wherein M is an alkali metal and Ac is an acetyl group.
* * * * *